US010319574B2

(12) United States Patent
Jo et al.

(10) Patent No.: US 10,319,574 B2
(45) Date of Patent: Jun. 11, 2019

(54) CATEGORIZATION DATA MANIPULATION USING A MATRIX-ASSISTED LASER DESORPTION/IONIZATION TIME-OF-FLIGHT MASS SPECTROMETER

(71) Applicants: Eung Joon Jo, Old Tappan, NJ (US); Yohahn Jo, Old Tappan, NJ (US)

(72) Inventors: Eung Joon Jo, Old Tappan, NJ (US); Yohahn Jo, Old Tappan, NJ (US)

(73) Assignee: Highland Innovations Inc., Old Tappan, NJ (US)

( * ) Notice: Subject to any disclaimer, the term of this patent is extended or adjusted under 35 U.S.C. 154(b) by 89 days.

(21) Appl. No.: 15/638,911

(22) Filed: Jun. 30, 2017

(65) Prior Publication Data

US 2018/0053642 A1 Feb. 22, 2018

Related U.S. Application Data

(60) Provisional application No. 62/377,768, filed on Aug. 22, 2016.

(51) Int. Cl.
| | |
|---|---|
| *H01J 37/317* | (2006.01) |
| *H01J 49/04* | (2006.01) |
| *G06N 20/00* | (2019.01) |
| *G06F 16/35* | (2019.01) |
| *H01J 49/00* | (2006.01) |
| *G06F 16/14* | (2019.01) |

(Continued)

(52) U.S. Cl.
CPC ........ *H01J 49/0418* (2013.01); *G06F 16/355* (2019.01); *G06N 20/00* (2019.01); *H01J 49/0036* (2013.01); *A61B 5/7246* (2013.01); *G06F 16/14* (2019.01); *H01J 49/26* (2013.01); *H01J 49/28* (2013.01)

(58) Field of Classification Search
CPC ........ H01J 49/00; H01J 49/02; H01J 49/0418; H01J 49/26; H01J 49/40; H01J 49/0027; H01J 49/0031; H01J 49/0036; G06K 9/00496
USPC ................................ 250/281, 282, 285, 288
See application file for complete search history.

(56) References Cited

U.S. PATENT DOCUMENTS

| 9,082,600 B1 | 7/2015 | Greving et al. |
| 2006/0003385 A1 | 1/2006 | Aguilera et al. |

(Continued)

FOREIGN PATENT DOCUMENTS

| WO | 2006/002415 A1 | 1/2006 |
| WO | 2016/094330 A2 | 6/2016 |

*Primary Examiner* — Jason L McCormack
(74) *Attorney, Agent, or Firm* — Daniel H. Sherr, Esq.

(57) ABSTRACT

Methods, systems, apparatuses, and/or computer programs. Mass spectrometer test data (e.g. a blood sample of a medical patient) may be associated with metadata information. The associated metadata information may be associated with the medical patient. A subset of a sample reference library may be based on the associated metadata information. The sample reference library may include a plurality of sets of mass spectrometer reference data, in accordance with embodiments. Embodiments match the mass spectrometer test data with mass spectrometer reference data of the selected subset of the sample reference library. Embodiments determine characteristic information of a source of the mass spectrometer test data (e.g. the medical patient) based on the known characteristics of the matched mass spectrometer reference data.

35 Claims, 15 Drawing Sheets

Figure 1:
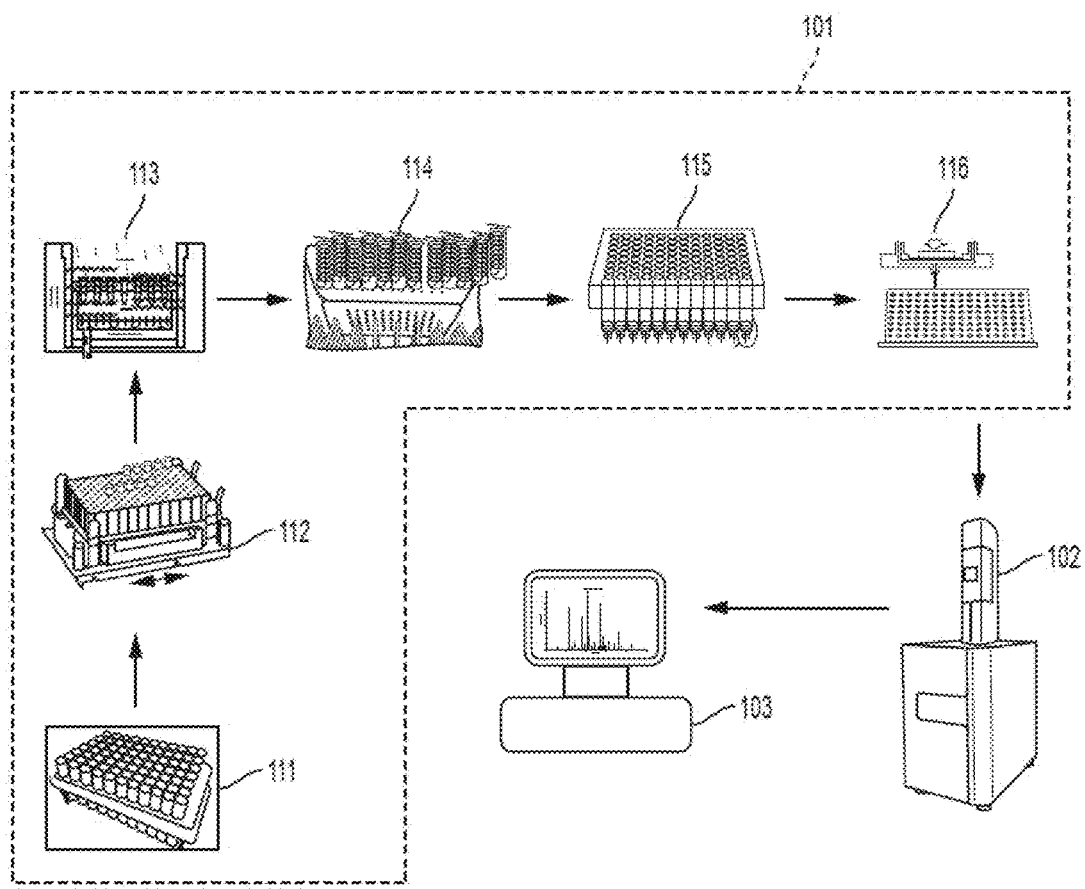

(51) Int. Cl.
*A61B 5/00* (2006.01)
*H01J 49/26* (2006.01)
*H01J 49/28* (2006.01)

(56) References Cited

U.S. PATENT DOCUMENTS

| | | | |
|---|---|---|---|
| 2007/0038387 A1* | 2/2007 | Chen | H01J 49/0036 |
| | | | 702/23 |
| 2009/0012723 A1 | 1/2009 | Treado et al. | |
| 2009/0179147 A1 | 7/2009 | Milgram et al. | |
| 2009/0256071 A1* | 10/2009 | Dantus | H01J 49/162 |
| | | | 250/282 |
| 2010/0332210 A1 | 12/2010 | Birdwell et al. | |
| 2011/0012016 A1* | 1/2011 | Maier | C12Q 1/04 |
| | | | 250/282 |
| 2012/0070044 A1 | 3/2012 | Avinash et al. | |
| 2013/0268212 A1* | 10/2013 | Makarov | H01J 49/025 |
| | | | 702/32 |
| 2014/0088885 A1 | 3/2014 | Lee | |
| 2016/0141164 A1 | 5/2016 | Kusch | |

\* cited by examiner

Figure 16

|     | C11  | C12  | C13  | C21  | C22   | C31   | C32   | C41  |
|-----|------|------|------|------|-------|-------|-------|------|
| C11 | 1.0  | 0.98 | 0.97 | 0.42 | 0.99  | 0.15  | 0.33  | 0.47 |
| C12 | 0.98 | 1.0  | 0.99 | 0.46 | 0.12  | 0.18  | 0.41  | 0.05 |
| C13 | 0.97 | 0.99 | 1.0  | 0.87 | 0.33  | 0.24  | 0.10  | 0.07 |
| C21 | 0.42 | 0.46 | 0.87 | 1.0  | 0.985 | 0.12  | 0.21  | 0.08 |
| C22 | 0.99 | 0.12 | 0.33 | 0.985| 1.0   | 0.087 | 0.09  |      |
| C31 | 0.15 | 0.18 | 0.24 | 0.12 | 0.087 | 1.0   | 0.995 |      |
| C32 | 0.33 | 0.41 | 0.10 | 0.21 | 0.09  | 0.995 | 1.0   |      |
| C41 | 0.47 | 0.05 | 0.07 | 0.08 |       |       |       | 1.0  |
| C42 | 0.98 |      |      |      |       |       |       |      |

CATEGORIZATION DATA MANIPULATION USING A MATRIX-ASSISTED LASER DESORPTION/IONIZATION TIME-OF-FLIGHT MASS SPECTROMETER

The present application claims priority to U.S. Provisional Patent Application No. 62/377,768 filed on Aug. 22, 2016, which is hereby incorporated by reference in its entirety.

BACKGROUND

A biomarker is a biological molecule found in blood, other body fluids, or tissues that is a sign of a normal or abnormal process of a condition and/or disease. For example, a glycoprotein CA-125 is a biomarker that may signal the existence of a cancer. Biomarkers may be measured and evaluated to identify the presence or progress of a particular disease or to see how well the body responds to a treatment for a disease or condition. Existence and/or a changes in quantity levels of biomarkers in proteins, peptides, lipids, glycan and/or metabolites may be measured by mass spectrometers.

Among numerous types of mass spectrometers, Matrix-Assisted Laser Desorption/Ionization Time-of-Flight Mass Spectrometry (MALDI-TOF MS) is an analytical tool employing soft ionization techniques. Samples may be embedded in a matrix and a laser pulse is fired at the mixture. The matrix absorbs the laser energy and the molecules of the mixture are ionized. The ionized molecules are then accelerated through a part of a vacuum tube by an electrical field and then fly in the rest of the chamber without fields. Time-of-flight is measured to produce the mass-to-charge ratio (m/z). MALDI-TOF MS offers rapid identification of biomolecules such as peptides, proteins and large organic molecules with very high accuracy and subpicomole sensitivity. MALDI-TOF MS may be used in a laboratory environment to rapidly and accurately analyze biomolecules and expanding its application to clinical areas such as microorganism detection and disease diagnosis such as cancers.

Complications may arise in comparing a test sample and reference data in order to efficiently and/or effectively characterize the test sample. For example, efficient and/or effective characterization of a test sample may substantially improve the utility of a Matrix-Assisted Laser Desorption/Ionization Time-of-Flight Mass Spectrometry, in accordance with embodiments.

SUMMARY

Embodiment relate to methods, systems, apparatuses, and/or computer programs. Mass spectrometer test data (e.g. a blood sample of a medical patient) may be associated with metadata information. The associated metadata information may be associated with the medical patient. Embodiments may select a subset of a sample reference library based on the associated metadata information. The sample reference library may include a plurality of sets of mass spectrometer reference data, in accordance with embodiments. Embodiments match the mass spectrometer test data with at least one set of the plurality of sets of mass spectrometer reference data of the selected subset of the sample reference library. Embodiments determine characteristic information of a source of the mass spectrometer test data (e.g. the medical patient) based on the known characteristics of the matched mass spectrometer reference data.

The mass spectrometer test data may include a mass-to-charge profile output of the mass spectrometer. The plurality of sets of mass spectrometer reference data comprises a plurality of mass-to-charge profiles of reference samples stored in the sample reference library. The matching comprises comparing the mass-to-charge profile of the mass spectrometer test data with the plurality of mass-to-charge profiles of the reference samples.

Embodiments relate to classification and/or categorization of reference data samples. Embodiments may improve identification and/or diagnostic accuracy because each category and/or classification is clustered with similar characteristics in order for clusters to be statistically independent from each other. In embodiments, clustering may allow a test sample to be matched and/or compared with its optimized category reference data in order to effectively and/or efficiently characterize the test sample.

DRAWINGS

Example FIG. 1 is an arrangement of a disease diagnosis laboratory where a sample processing unit, a MALDI-TOF MS unit, and a diagnosis unit are separated in three different systems, in accordance with embodiments.

Figure 2:
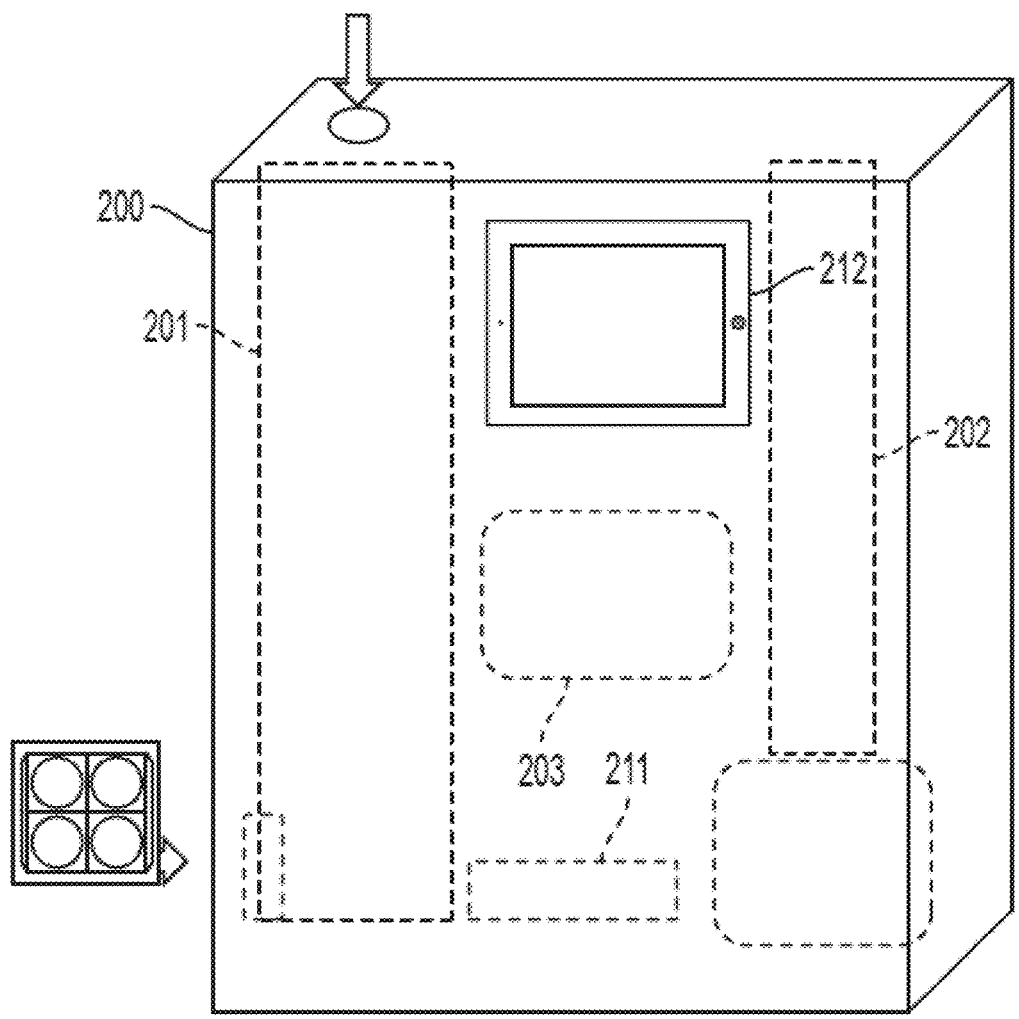

Example FIG. 2 is a system diagram including a sample processing unit, a MALDI-TOF MS unit, and a diagnosis unit integrated into one system, in accordance with embodiments.

Figure 3:
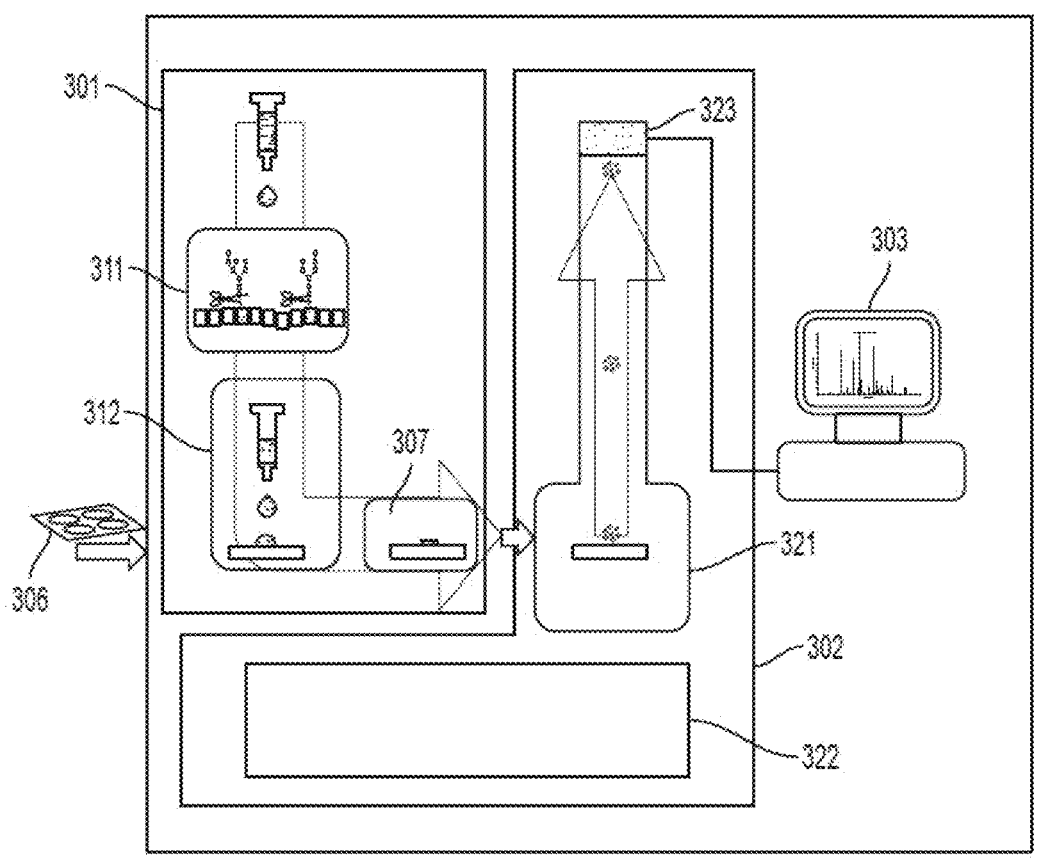

Example FIG. 3 is a system diagram of the integrated system including a sample processing unit, a MALDI-TOF MS unit, and a diagnosis unit in one system, in accordance with embodiments.

Figure 4:
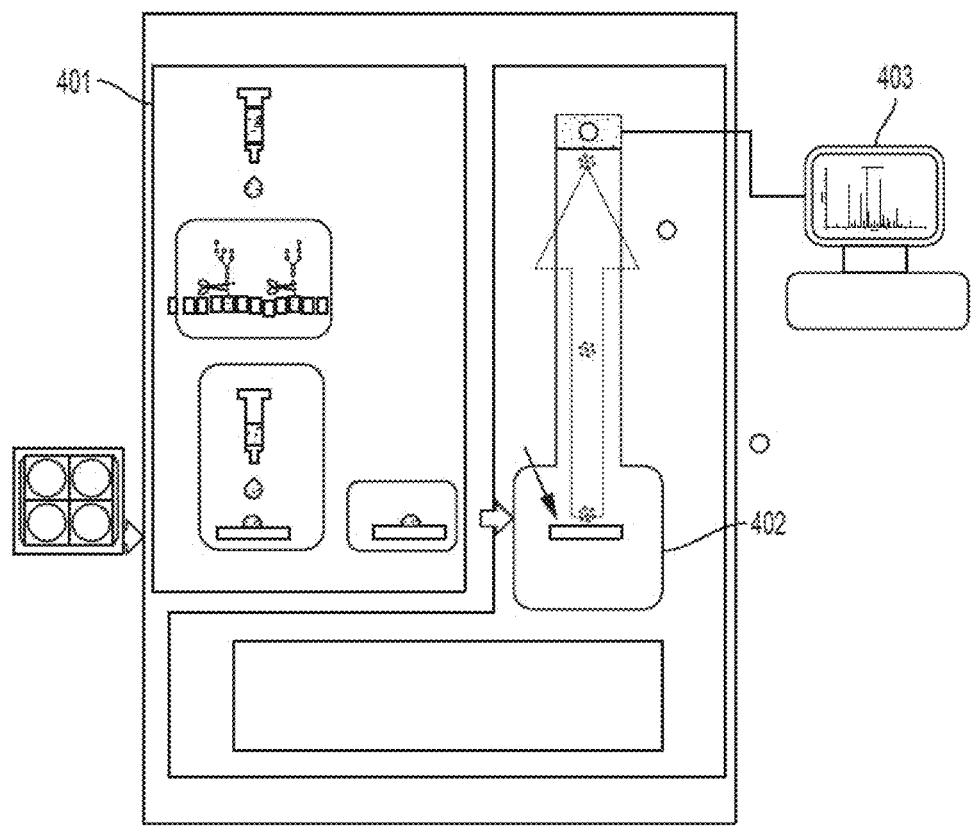

Example FIG. 4 is a system diagram of an integrated diagnostic system including a sample processing unit and a MALDI-TOF MS unit integrated in one system, whereas a diagnosis unit is provided as a separate unit, in accordance with embodiments.

Figure 5:
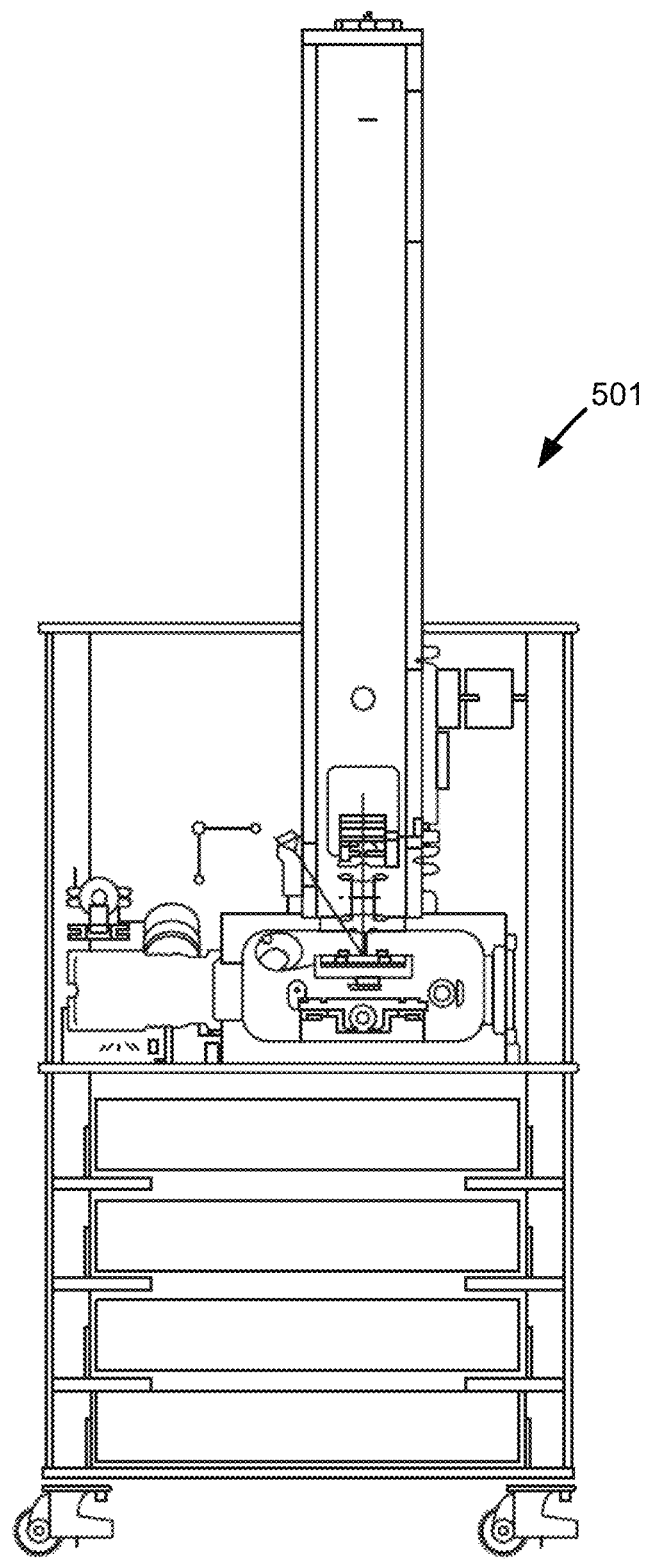

Example FIG. 5 is a schematic view of a MALDI-TOF MS unit in which components are in modules, in accordance with embodiments.

Figure 6:
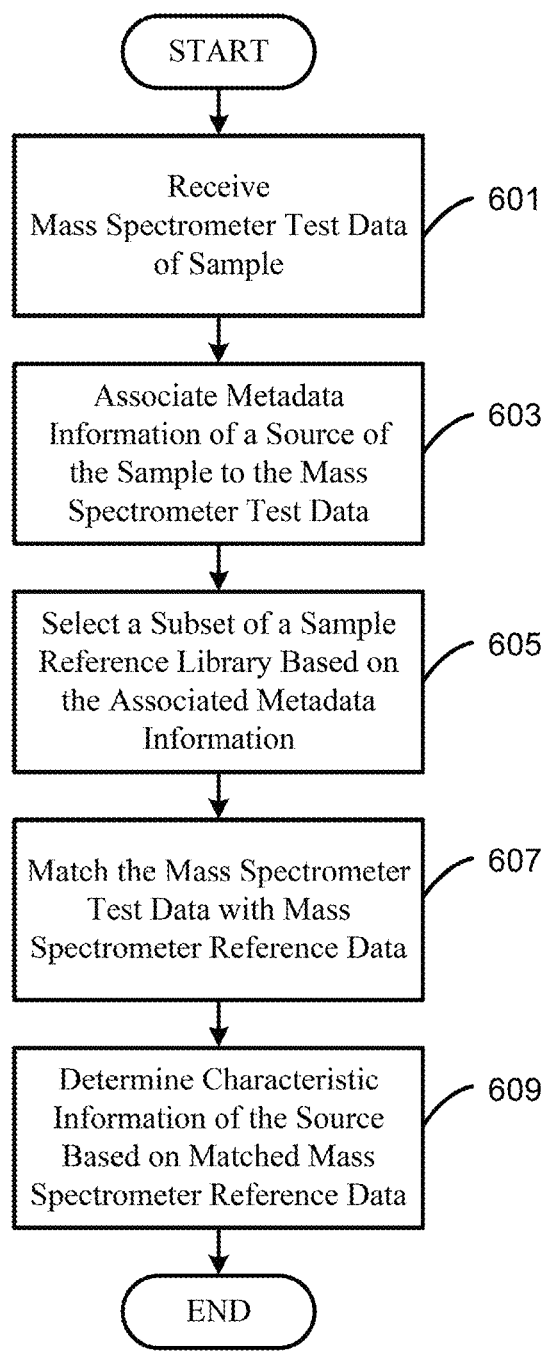

Example FIG. 6 is a flow chart of a method to match characteristic information, in accordance with embodiments.

Figure 7:
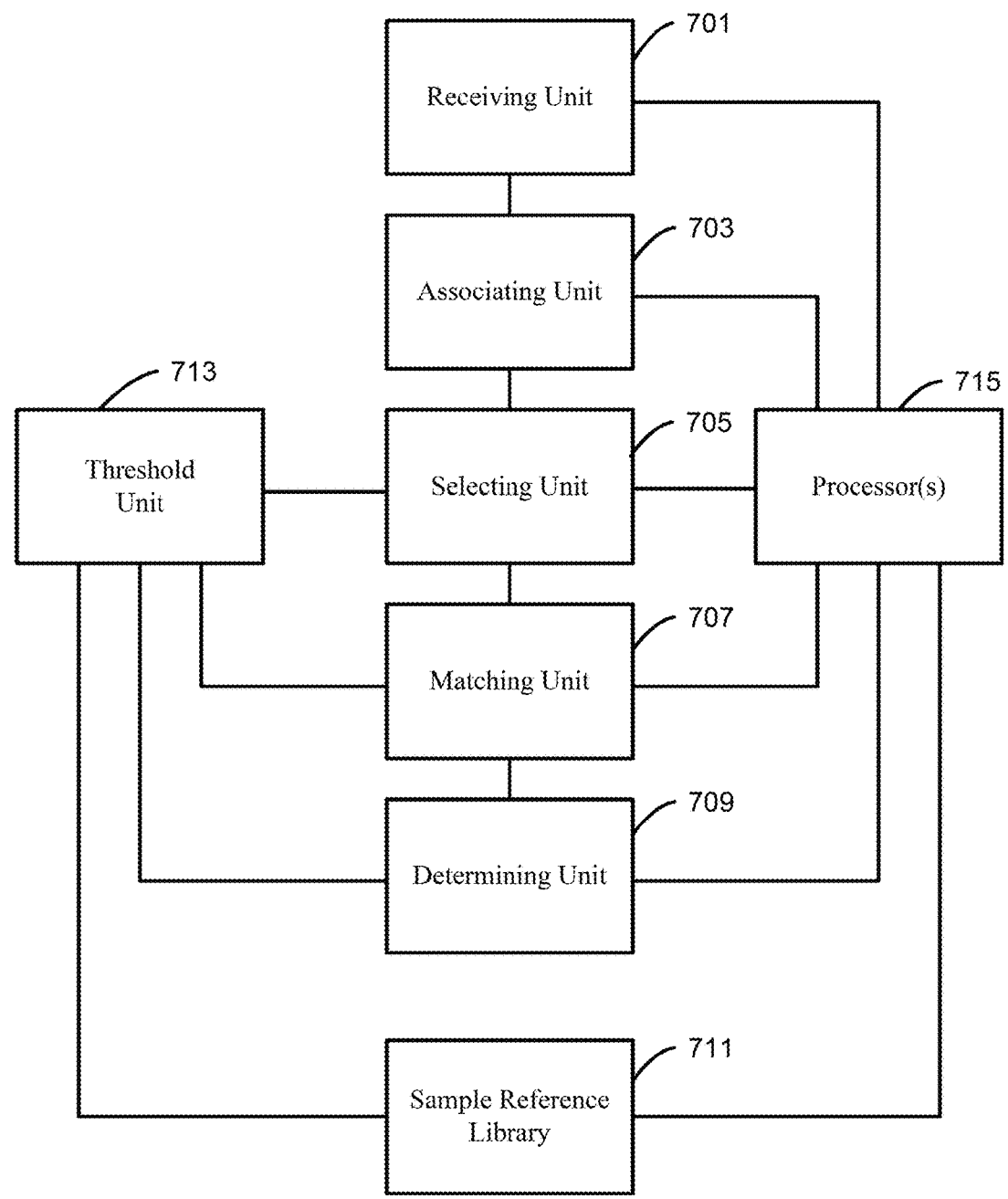

Example FIG. 7 illustrates a system for matching characteristic information, in accordance with embodiments.

Figure 8:
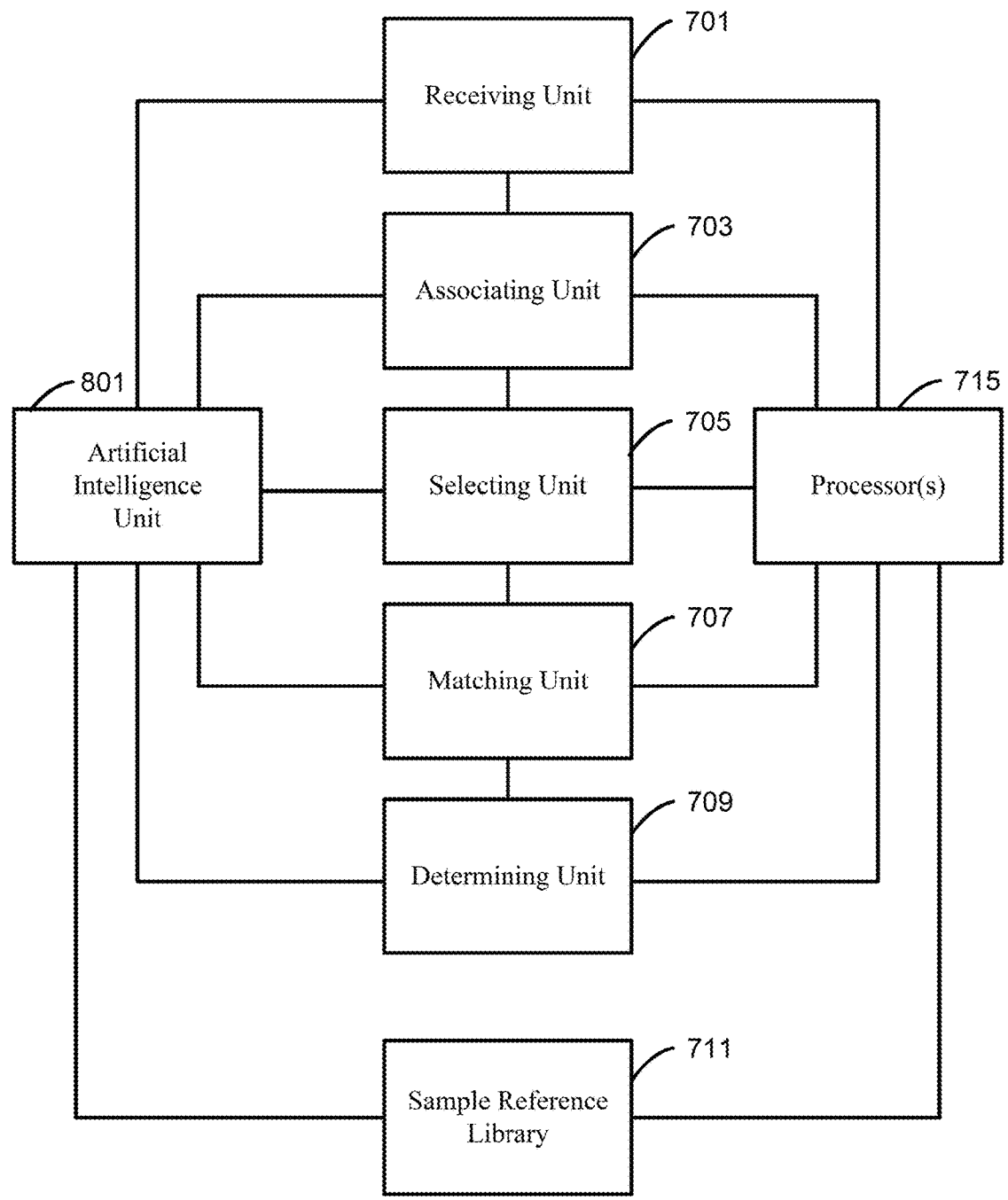

Example FIG. 8 illustrates a system for matching characteristic information using artificial intelligence, in accordance with embodiments.

Figure 9:
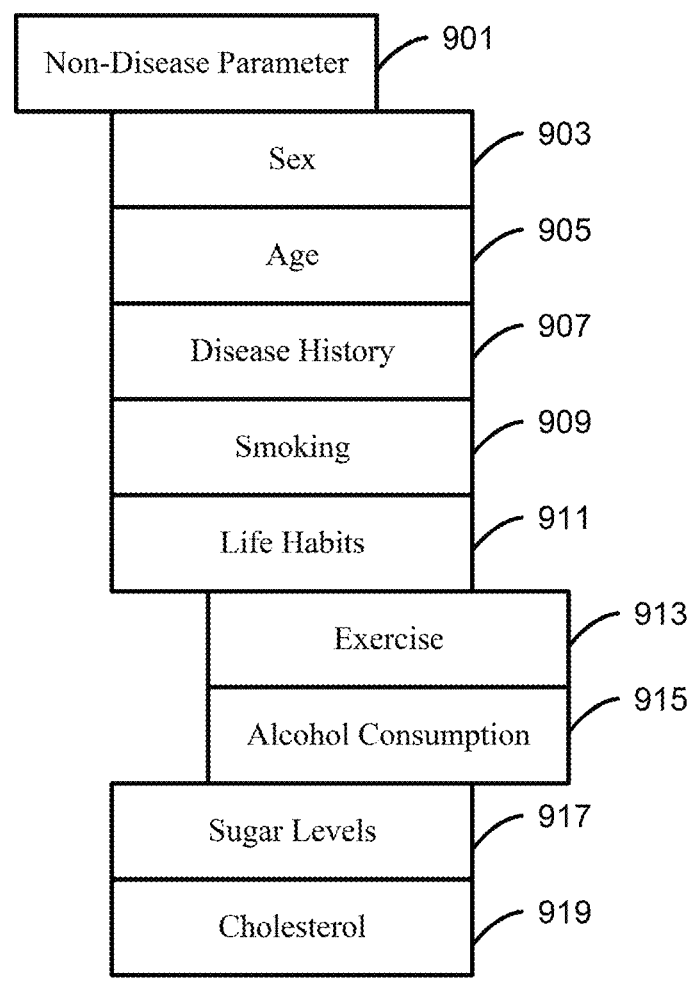

Example FIG. 9 illustrates a hierarchy of parameters and sub-parameters, in accordance with embodiments.

Figure 10:
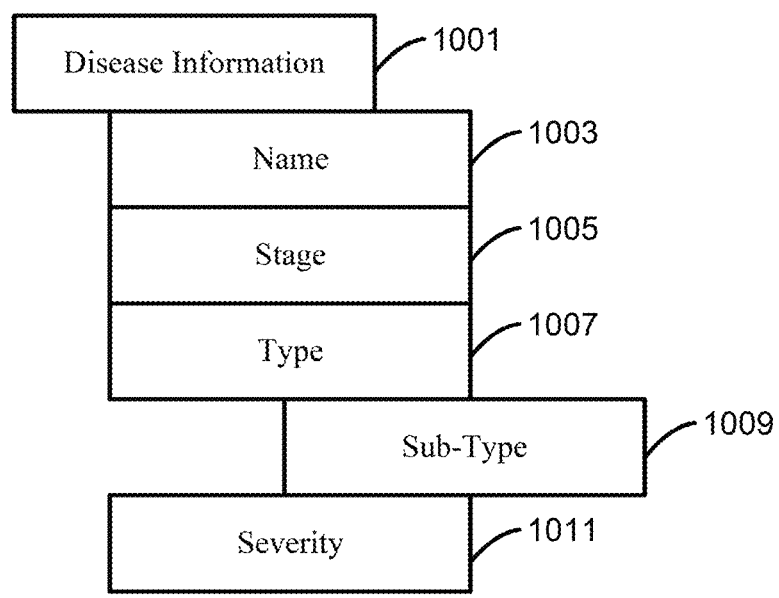

Example FIG. 10 illustrates a hierarchy of disease information, in accordance with embodiments.

Figure 11:
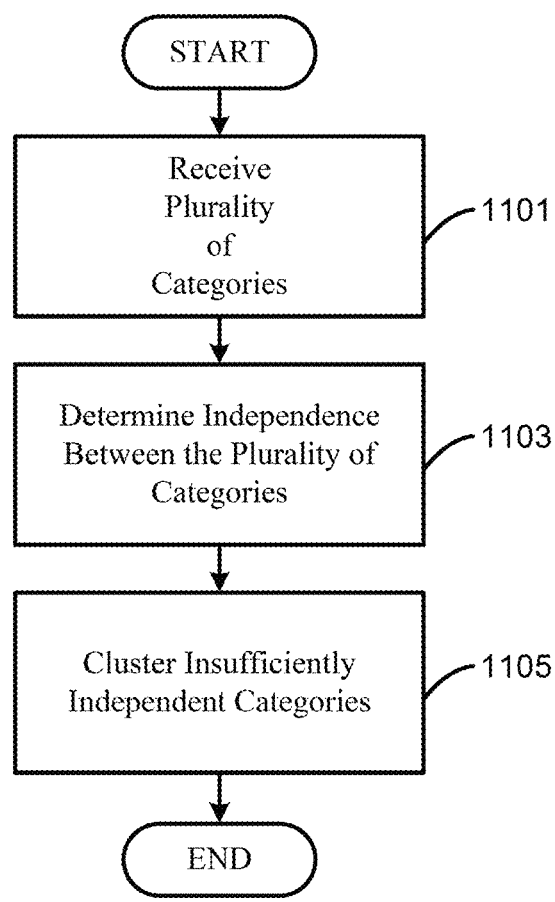

Example FIG. 11 illustrates a method of determining independence between categories, in accordance with embodiments.

Figure 12:
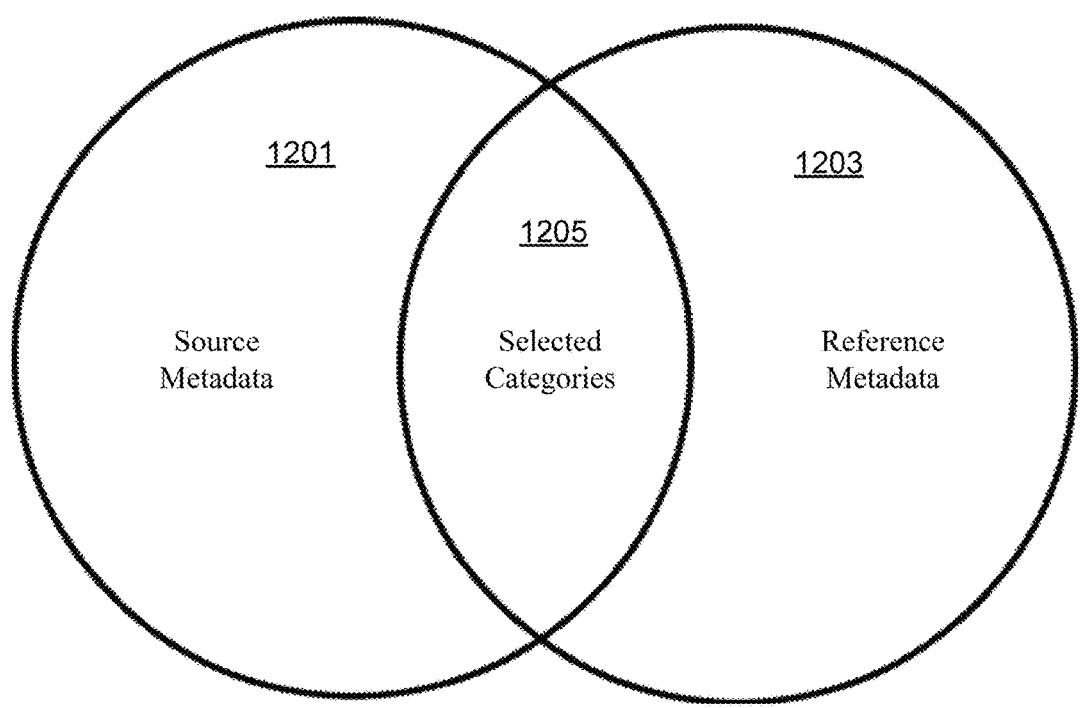

Example FIG. 12 illustrates a cross-section between source metadata and reference metadata, in accordance with embodiments.

Figure 13:
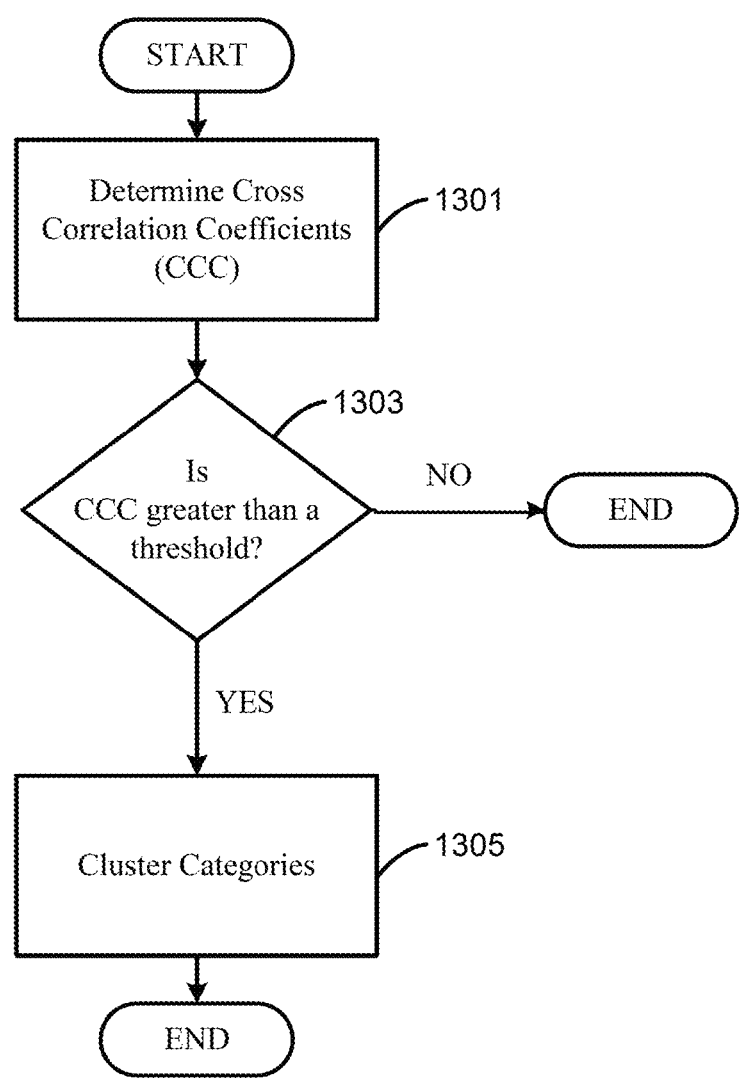

Example FIG. 13 illustrates a method of clustering categories, in accordance with embodiments.

Figure 14:
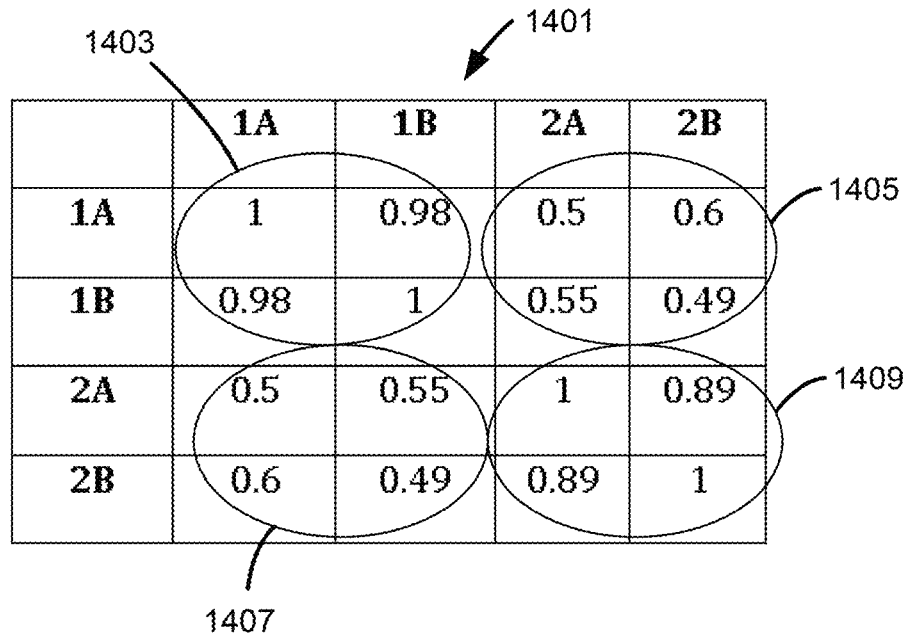
Figure 15:
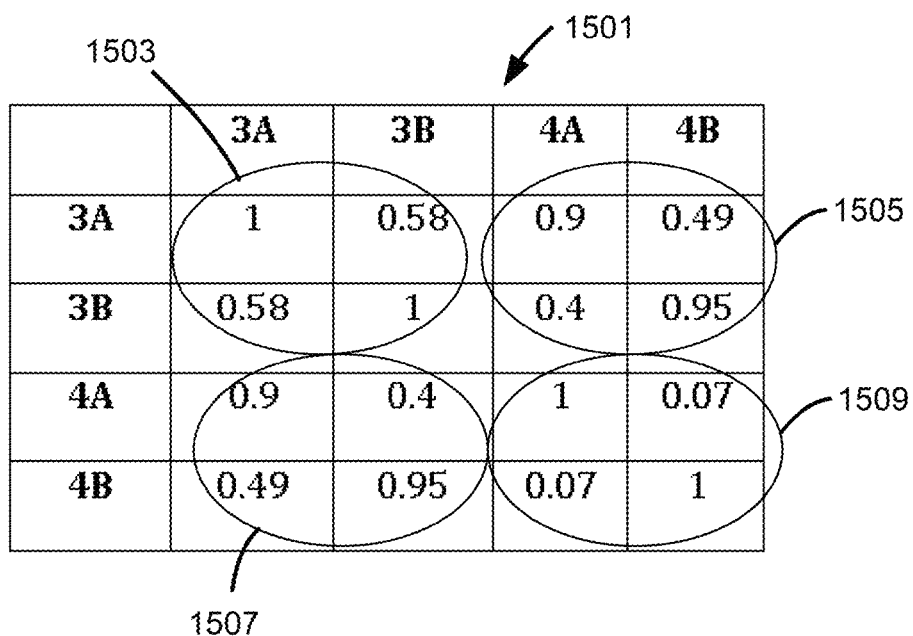

Example FIGS. 14 through 16 illustrate examples of clustered categories, in accordance with embodiments.

DESCRIPTION

Example FIG. 1 illustrates a disease diagnosis laboratory where a sample processing facility 101 includes multiple sample processing tools, a MALDI-TOF MS system 102, and a diagnosis software system 103, which are separated from each other, in accordance with embodiments. To extract a glycan for an ovarian cancer diagnosis, for example, a patient's serum is entered into a multi-well plate 111 to undergo a sample reception process and a protein denaturation process 112, followed by a deglocosylation process using enzyme 113. A protein removal process 114, a drying and centrifugation process, a glycan extraction process 115, and a spotting process 116 then follow. The spotted samples are analyzed by the MALDI-TOF MS system 102 to generate at least one glycan profile. The diagnosis software 103 compares the glycan profile of the sample with the pre-stored glycan profile or profiles to identify the presence and progress of ovarian cancer.

Example FIG. 2 shows an integrated disease diagnosis system using MALDI-TOF, in accordance with embodiments. The system 200 includes of an automatic sample preparation unit 201, a MALDI-TOF MS unit 202, and a disease diagnosis unit 203, all integrated into one integrated system. The sample preparation unit 201 prepares a patient's sample, which are transferred to the MALDI-TOF MS unit 202 through automatic transporting means such as a conveyor 211. The MALDI-TOF MS unit 202 analyzes the sample and generates the mass information of the sample. The disease diagnosis unit 203 then identifies the presence and progress of the disease, and show the result in the monitor screen 212.

Embodiments identifies the existence and quantity variations of proteins, RNAs, DNAs in blood, urine, and other biomaterials such as microorganisms, in an autonomous manner by touching input monitor screen only 212. Embodiments may be used to identify diseases including cancers and microorganisms such as bacteria, archaea, protozoa, viruses, and fungi.

Example FIG. 3 shows the integrated disease diagnosis system, in accordance with embodiments. Samples may undergo a combination of process by selected modules. In the sample preparation system 301, a sample goes through a predefined and preprogrammed sequence depending on diagnosis or screening purposes in an automatic sample preparation unit 311. In embodiments, for glycan extraction, multiple processing modules may be selected, which as sample reception, protein denaturation, deglycosylation, protein removal, drying, centrifugation, solid phase extraction, and/or spotting. After sample preparation, the sample loader 312 loads the samples onto the plates 306 and are dried in a sample dryer 307.

The samples may then be provided to the MALDI-TOF MS unit 302 having a ion flight chamber 321 and/or a high voltage vacuum generator 322, in accordance with embodiments. A processing unit 323 in the MALDI-TOF MS may identify the mass/charge and its corresponding intensity. For the disease diagnostic purpose, those acquired mass and intensity data may be reorganized to set up a standard mass list, in which a concept of the center of mass where intensities are balanced and equilibrated is introduced. A standard mass to charge list is defined based upon the machine accuracy and the center of mass concept. The stored spectrum data for each laser irradiation may also be used to set up the standard mass list.

In embodiments, diagnostic unit 303 may then compare, the spectra from a patient's sample with the pre-stored spectra and analyzes the pattern difference of the two spectra. The diagnostic unit 303 may then identify the presence and progress of the disease. In embodiments, as shown in example FIG. 3, diagnostic unit 303 may be internally integrated to the MALDI-TOF MS unit 302. In embodiments, diagnostic unit 303 may be either internal or external to a mass spectrometer system. In embodiments, a diagnostic unit may be cloud based. In embodiments, a diagnostic unit may be networked to a mass spectrometer system by a local network (e.g. an intranet network), a public network (e.g. the internet), or any other network as appreciated by those skilled in the art. In embodiments, a diagnostic unit may be coupled to an artificial intelligence engine and/or to one or more processors that implement deep learning algorithms.

Example FIG. 4 illustrates an integrated disease diagnosis system where the sample preparation unit 401 and the MALDI-TOF 402 are integrated, with the diagnosis unit 403 stands apart as a separate unit, in accordance with embodiments. Example FIG. 5 is a schematic view of a MALDI-TOF MS unit in which components are in modules, in accordance with embodiments.

Example FIG. 6 is a flow chart of a method to match characteristic information, in accordance with embodiments. Embodiments relate to at least one of a method, apparatus, system, and/or computer program product. At step 601, embodiments may receive mass spectrometer test data of a sample. At step 603, embodiments may associate metadata information of a source of the sample to the mass spectrometer test data. At step 605, embodiments may select a subset of a sample reference library based on the associated metadata information. The sample reference library may include a plurality of sets of mass spectrometer reference data, in accordance with embodiments. At step 607, embodiments may match the mass spectrometer test data with at least one set of the plurality of sets of mass spectrometer reference data of the selected subset of the sample reference library. At step 609, embodiments may determine characteristic information of the source based on the known characteristics of the matched mass spectrometer reference data.

In embodiments, the mass spectrometer test data comprises a mass-to-charge profile output of the mass spectrometer. The plurality of sets of mass spectrometer reference data may include a plurality of mass-to-charge profiles of reference samples stored in the sample reference library. The matching 607 may include comparing the mass-to-charge profile of the mass spectrometer test data with the plurality of mass-to-charge profiles of the reference samples.

The matching 607 may include deciding to match the mass spectrometer test data with a set of the plurality of sets of mass spectrometer reference data if there is substantially similar mass-to-charge profiles, in accordance with embodiments. In embodiments, the deciding to match the substantially similar mass-to-charge profiles may be performed according to predetermined thresholds. In embodiments, the deciding to match the substantially similar mass-to-charge profiles may be performed according to dynamic thresholds. In embodiments, the dynamic thresholds are determined by at least one of artificial intelligence or deep learning algorithms.

Example FIG. 7 illustrates a system for matching characteristic information, in accordance with embodiments. A system may include at least one processor 715. A system may include a receiving unit 701 configured to receive mass spectrometer test data of a sample using the at least one processor 715. A system may include an associating unit 703 configured to associate metadata information of a source of the sample to the mass spectrometer test data using the at least one processor 715. A system may include a selecting unit 705 configured to select a subset of a sample reference library based on the associated metadata information using the at least one processor 715. The sample reference library 711 may include a plurality of sets of mass spectrometer reference data. A matching unit 707 may be configured to match the mass spectrometer test data with at least one set of the plurality of sets of mass spectrometer reference data of the selected subset of the sample reference library 711 using the at least one processor 715. A determining unit 709 may be configured to determine characteristic information of the source based on the known characteristics of the matched mass spectrometer reference data using the at least one processor 715.

In embodiments, mass spectrometer test data may have unknown characteristics and a plurality of sets of mass spectrometer reference data has known characteristics. The sample may include biological molecules. The metadata information of the source may include information about the source of the biological molecules. The characteristic information of the source may include a biological analysis information of the source. The biological analysis information may be a medical diagnosis of at least one of a human being, an animal, a plant, or a living organism.

Example FIG. 8 illustrates a system for matching characteristic information using artificial intelligence, in accordance with embodiments. For example, artificial intelligence unit 801 may be coupled to receiving unit 701, associating unit 703, selecting unit 705, matching unit 707, determining unit 709, sample reference library 711, processor(s) 715, and/or any other unit of a system in order to optimize efficiency and/or effectiveness of a system.

Example FIG. 9 illustrates a hierarchy of parameters and sub-parameters, in accordance with embodiments. In embodiments, metadata information of a source and a metadata information of the plurality of sets of mass spectrometer reference data may include a plurality of categories having parameters. In embodiments, categorization information may include at least one non-disease parameter. The sample reference library is stored in at least one of a MALDI-TOF MS machine, a hard drive, or a cloud database. The at least one non-disease parameter comprises attributes of the source.

The at least one non-disease parameter 901 may include at least one of an indication of: A sex 903 of the source. An indication of an age 905 of the source. An indication of a disease history 907 of the source. An indication of a family disease history of the source. An indication of a smoking history 909 of the source. An indication of life habits 911 of the source. An indication of exercise habits 913 of the source. An indication of a drinking history 915 of the source. An indication of sugar levels 917 of the source. An indication of cholesterol levels 919 of the source. The at least one non-disease parameter may include at least one sub-parameter describing at least one attribute of the at least one non-disease parameter.

Example FIG. 10 illustrates a hierarchy of disease information 1001, in accordance with embodiments. The disease information 1001 relates to a disease and the disease information comprises at least one parameter or sub-parameter relating to at least one of a name of the disease 1003, a time stage of the disease 1005, a type of the disease 1007, a sub-type of the type of the disease 1009, severity of the disease 1011, and/or information relating to the disease. In embodiments, characterization information of the source may include at least one disease parameter. In embodiments, at least one disease parameter may be a correlation of disease information to the source of the biological molecules.

Example FIG. 11 illustrates a method of determining independence between categories, in accordance with embodiments. In embodiments, a plurality of categories may be received 1101. In embodiments, relative independence of the plurality of categories may be determined 1103. In embodiments, insufficiently independent categories may be clustered.

Example FIG. 12 illustrates a cross-section between source metadata 1201 and reference metadata 1203, in accordance with embodiments. The selecting the subset 1205 of the sample reference library comprises determining overlap between the associated metadata information of the source 1201 and metadata information of the plurality of sets of mass spectrometer reference data 1203. In embodiments, the correlation between the plurality of categories may be minimized in order to maximize independence of each of the plurality of categories.

Example FIG. 13 illustrates a method of clustering categories, in accordance with embodiments. In step 1301, embodiments may determine cross correlation coefficients (CCC) between two categories. In decision step 1303, it may be determined if the determined cross correlation coefficients are greater than a threshold. If cross correlation coefficients are greater than a threshold, then those categories may be clustered, in accordance with embodiments. If cross correlation coefficients are less than a threshold, then the process may end without clustering the two categories.

In embodiments, eliminating irrelevant sets of the plurality of sets of mass spectrometer reference data may include clustering categories of the plurality of categories that are not sufficiently independent to minimize size of the sample library. In embodiments, clustering may include determining at least one cross-correlation coefficient between at least two of the plurality of categories. If the at least one cross-correlation coefficient is greater than a predetermined threshold for the at least two of the plurality of categories, then clustering the at least two of the plurality of categories together to minimize the size of the sample library, in accordance with embodiments.

The clustering categories may include intra-category clustering at least two subcategories of one of the plurality of categories, in accordance with embodiments. The clustering categories may include inter-category clustering of at least two subcategories of different categories of the plurality of categories, in accordance with embodiments. In embodiments, a predetermined threshold of the at least one cross-correlation coefficient is greater for intra-category clustering than for inter-category clustering.

In embodiments, independence of each of the plurality of categories may be based on at least one of a minimum independence threshold, a correlation coefficient index, a cross correlation index, a relative standard deviation analysis, or a distinction threshold to obtain a predetermined degree of diagnostic accuracy. In embodiments, independence of each of the plurality of categories is determined by a dynamic threshold. In embodiments, a dynamic threshold may be determined by at least one of artificial intelligence or a deep learning algorithm.

In embodiments, independence of each of the plurality of categories is determined based on a relative standard deviation value. In embodiments, the relative standard deviation value may be at least one of minimized or optimized to maximize at least one of reproducibility or accuracy.

In embodiments, independence of each of the plurality of categories optimizes the selecting the subset of the sample library. In embodiments, a subset of the sample library may be optimized by at least one of minimizing the size of the subset of the sample library or maintaining a predetermined degree of diagnostic accuracy. In embodiments, a subset of the sample library is optimized by eliminating irrelevant sets of the plurality of sets of mass spectrometer reference data.

In embodiments, irrelevant sets may include sets of mass spectrometer reference data which have a risk of false positive or false negative output results based on the associated metadata information of the source. In embodiments, irrelevant sets comprise sets of mass spectrometer reference data which are mutually exclusive to the associated metadata information. In embodiments, correlation between the plurality of categories may be determined from at least one of artificial intelligence or a deep learning algorithm. In embodiments, correlation between the plurality of categories is minimized to optimize at least one of diagnosing, screening, or identifying a medical condition.

FIG. 14 is an illustrative example in accordance with embodiments where the samples are initially categorized by the numbers. The intra-correlation between 1A and 1B (0.98) is higher than the inter-correlation between 1A and 2A (0.5), which may indicate that the samples are properly categorized, in accordance with embodiments. For example, all of the values in clusters 1403 and 1409 have substantially high values when correlated against each other. Conversely, clusters 1407 and 1405 have relatively low values when correlated against other clusters, demonstrating a hypothetical effective clustering in accordance with embodiments.

FIG. 15 illustrates an example in accordance with embodiments where the samples are initially categorized by the numbers. The intra-group correlation between 3A and 3B (0.58), lower than the inter-group correlation between 3A and 4A (0.9) indicating that the initial categorization may not be optimal or ideal. In embodiments, artificial intelligence may re-categorize and/or recluster, in accordance with embodiments. For example clusters 1503, 1505, 1507, and 1507 of hypothetical map 1501 are relatively uncorrelated.

In embodiments, elements in a category may not necessarily be fixed. Instead, a computer program may be used to find an optimal set of elements to be included in the category, in accordance with embodiments.

FIG. 16 illustrates an example 1601 in accordance with embodiments where samples are initially categorized into clusters C1X (e.g. cluster 1603), C2X (e.g. cluster 1609), and C3X (e.g. cluster 1611). In this example, in accordance with embodiments, all the intra-CCC within cluster 1X are between 0.97 and 1.0, which may indicate a relatively high correlation in cluster 1603. However, in embodiment the inter-CCC of C1X (e.g. cluster 1603) and C2X (such as the inter-CCC between C11 and C22) is higher than the minimum of intra-CCC of C1X (0.97). This may indicate a categorization error in selecting elements for cluster 1603 or cluster 1609 as shown in the mis-clustering due to correlation 1605 or correlation 1607 being relatively high at 0.99. In accordance with embodiments, a false negative or false positive result may be caused at category C22 (e.g. 0.99).

Embodiments relate to clustering-based categorization possibly requiring more specific information about sub-categories such as stages of cancers rather than simple binary sample information such as cancer versus normal healthy. Once the optimal categorization and/or group is found, an average or a median of the category may be found to set the statistical standards for each categories and its distribution curve, in accordance with embodiments.

In embodiments, manipulated mass spectrometer data may be compared to data stored in a library database. Rather than comparing a test sample to the known samples one by one as in target diagnosis, the test sample may be compared to an entire database of known and defined samples. Embodiments may increase efficiency and/or reduce the chance of a false positive or false negative diagnosis. Test sample data may be pre-categorized against a library database to further create parameters that can expedite, increase the accuracy of, and/or otherwise improve the disease identification process. The categorization analysis may be based on clustering analysis, in accordance with embodiments. A library database itself may be integrated into the MALDI-TOF MS machine, stored in software or hard-drives, and/or stored in a cloud database.

Embodiments relate to disease diagnosis and screening. The underlying assumption of this method is that every person, even those that are presumably healthy, has some sort of disease or precursor such as diabetes, high-cholesterol, Alzheimer's disease, cancers, contagious disease, etc., in accordance with embodiments. Therefore, every person may be regarded at least as a potential patient, in accordance with embodiments. Additionally, embodiments may regard every status or stage of a disease or non-disease related parameter as unique and differentiable.

In embodiments, every person/animal/plant/etc. may be divided into categorizations consisting of either disease and/or non-disease parameters. For instance, a categorization may consist of a disease-related parameter that differentiates between cancers such as ovarian, lung, brain, etc., in accordance with embodiments. Assuming that it is determined that the test sample is determined to be an ovarian cancer, another more specific parameter can distinguish between ovarian cancer stages (benign, borderline, I, II, III, and IV), in accordance with embodiments. Embodiments may include parameters that are even more specific and may differentiate ovarian cancer types such as epithelial, germ-cell, or stromal. Embodiments may include parameters that may differentiate between the patient/sample's cholesterol level (>200 mg/dl, >250 mg, <200 mg). Other aspects such as ethnicity, age, previous disease history, and life habits can also be used as categorization parameters, in accordance with embodiments. In embodiments, a test sample may be initially identified with a category of combined parameters such as ovarian cancer—stage I—epithelial—>200 mg cholesterol—age 20-30—etc. After the particular category of combined parameters best representing the test sample is selected, its MALDI-TOF MS data may be compared with and screened against the data stored in the library database for the same parameters, in accordance with embodiments.

The nature of categorizations composed of variable parameters may give many different means of finding the optimum categorization for disease diagnosis/screening/identification. Embodiments may optimize the categorization of a sample by minimizing the correlation between categorizations consisting of different parameters to ensure independency of the categorizations. For example, the cross correlation index or the norm of the MALDI-TOF MS intensity profiles between a particular categorization and different categorizations may have to be small enough to be within a distinction threshold, in accordance with embodiments. This distinction threshold can be something like a minimum/optimal RSD (Relative Standard Deviation) value to maximize reproducibility and accuracy of mass/intensity data. Embodiments may use other accuracy criteria such as maximum specificity/sensitivity values. The categorization or clustering can be optimized by using intra- and inter-category similarity comparison, in which intra-correlation among sample data in a category should be greater than inter-correlation.

In embodiments, categorizations may be divided into two broad principal categories. Category I may comprise non-disease related categorizations and category II may comprise disease-related categorizations, in accordance with embodiments. For category I, 5-10 parameters may be used as an illustrative example. Embodiments may include non-disease related parameters such as sex, age, family history, smoking, alcohol consumption, blood sugar, and cholesterol. Each of these parameters may be further divided into a number or numbers of sub parameters, in accordance with embodiments. In embodiments, the number of principal categories may be determined by various methods, but a deep-learning AI based system is suggested for greatest accuracy. In embodiments related to deep-learning based systems, the relative standard deviation of the data (for instance MALDI-TOF MS profile data) for each proposed category may be minimized. Some embodiments related to deep-learning based systems may have the correlation coefficient index of the relative standard deviation of the data kept at a minimum, maximum, or recommended value of detection accuracy like specificity and/or sensitivity. In embodiments, other accuracy parameters may be maximized through the machine algorithm to avoid missing an optimized cluster of categories and/or to save time of finding categorization process.

In embodiments, categorization may be illustrated with the following example in which a categorization is constructed:

Category I (Non-Disease)

Parameter 1: Sex {Male, Female, Other} . . . {Male, Female}

Parameter 2: Age {0-15, 16-30, 31-45, 46-60, 61-75, 76 and over} . . . {0-20, 21-40, 41-60, over 60}

Parameter 3: Family Disease History {Cancer, Diabetes, Alzheimer, None} . . . {Cancer, Non-cancer} . . . { }

Parameter 4: Smoking{Heavy(>1 pack), Light(<1 pack), Non-smoking} . . . {Smoking, Non-smoking} . . . { }

Parameter 5: Drinking {Heavy, Light, no-drink} . . . {Drinking, Non-drinking} . . . { }

Parameter 6: Sugar {Diabetes level, Low-level, No-diabetes} . . . {Diabetes level}

Parameter 7: Cholesterol {High, Medium, Low} . . . {Hyperlipidemia, Normal}

In this example, the non-disease related category I would have 5832 possible (=3*6*4*3*3*3*3) subcategories, or as described above, categorizations, in accordance with embodiments. A sample categorization (one of 5832 possible permutations) is {Male, 31-45 ages, Family History of Cancer, Light Smoker, No Diabetes, Low Cholesterol Level}.

Since one goal of categorization is to improve the accuracy of library based diagnostics, each categorization in turn may be required to be sufficiently distinct from one another, in accordance with embodiments. Embodiments may look at the lowest correlation of the MALDI-TOF distribution data between 2 categorizations and/or the lowest correlation amongst more than 2 categorizations to determine the distinction between categorizations. By setting a threshold minimum independency between categorizations with the purpose of obtaining a sufficient degree of diagnostic accuracy, categorizations may be grouped and/or eliminated since they are too similar to be of use, in accordance with embodiments. In this way, a theoretical library of thousands of categorizations can be reduced to a smaller number of sufficiently distinct categorizations, in accordance with embodiments.

Embodiments relate to the obtaining of p-values or cross-correlation coefficients obtained from MALDI-TOF MS data such as m/z versus intensity to determine this threshold minimum independency value. These distinction parameters (whether p-value or cross-correlation coefficient) may be obtained for each sub-categorization and the parameters can be compared determine a threshold value or ranges, in accordance with embodiments. Embodiments relate to the determination and storage of distinction parameters in the library database for each biomarker (such as glycans, proteins, RNAs, DNAs, lipids, etc.) associated with a particular sub-categorization or disease.

Embodiments relate to the matching of test sample data with the data stored in the database utilizing an established library database of sufficiently distinct subcategories in order to obtain accurate disease diagnostics. Embodiments may not use test diagnostics in which the mass spectrum data of the test sample is compared to individual subset or category of samples in the database in order to come to match. Embodiments relate to the comparing of the data from the test sample with the data of all the diseases and statuses stored in a pre-categorized library database. Modified cross-correlation technique may be used in which the standard m/z data from the database is retrieved and then matched with the intensity data obtained from the MALDI-TOF MS, in accordance with embodiments. In embodiments, the degree of matching will be calculated as norm or similarity values determined from correlation coefficients.

The specific matching process may be intensive, but may potentially be inefficient if every single database disease/status is compared to the test sample being analyzed. To cut down on this inefficiency, embodiments may involve the matching of non-disease characteristics of the test sample with those stored in the database. For example, if we know that the test sample came from a female smoker with a family history of diabetes, embodiments may limit the matching of the test sample data with only the data stored in the library database for the corresponding categorization (i.e. Female—smoker—family history of diabetes—etc.). After this initial screening process, the data for the disease-related categorizations (i.e. ovarian cancer—epithelial—stage III) may be matched the standardized m/z data of the test sample and the closest match may be determined to be the identity of the disease or status in question, in accordance with embodiments. The matching without categorization may also be performed for further comparison of accuracy or efficiency.

In some embodiments, the reference data may be categorized first to minimize the correlation process between and among categories. At the same time, the non-disease categories of the test sample may be determined, in accordance with embodiments. Afterwards, the database for disease categories may be matched with the test sample data, and this may save cost and time of the identification process, in accordance with embodiments.

In embodiments, the data of a test sample may be first compared with subcategories of Category I (non-disease) to find out which population/non-disease categorization should be applied.

In embodiments, each mass-to-charge (m/z) of the test sample may next be standardized and matched with the MALDI spectrum data in the disease database. Many algorithms for matching can be used to find the best match between the test sample data and the database data to find the specific disease category, in accordance with embodiments.

There may be multiple ways in which categorization can lead to more efficient database based diagnostics. In embodiments, certain restraints or thresholds may be required to be applied to ensure that the pre-defined categorization does not reduce diagnostic accuracy. Pre-defined categorization may have usefulness for database based matching diagnostics, in accordance with embodiments. In some embodiments, as the database grows with increased sample data, algorithms and deep learning based programs can continually improve categorization until the optimum categorizations may be determined for the person whose sample is being tested, the disease type for which the sample is being screened, and other possible discernible parameters/characteristics.

In embodiments, mass spectrum data from unknown samples may be compared with the mass profiles of mass spectrum data stored in the library database to identify a disease or the progress of a disease. The mass profiles may be categorized or grouped into categories to be stored in the library database, in accordance with embodiments. In embodiments, cross correlation and/or correlation coefficients and similarity index may be calculated between the unknown sample and the standard mass profiles of all possible categories in order to match an unknown sample with one in the library database. Based on the computed cross correlation values, a disease or the progress of a disease may be identified, in accordance with embodiments.

In order to get a higher accuracy for identification or diagnosis, a proper categorization may be necessary. In embodiments, pre-defined categories based on the available information disclosed. For patient identification, a patient can be divided by age, sex, presence of other diseases, and many others, in accordance with embodiments.

Embodiments relate to defining new categories using an analytical method for general applications. Cross-correlation values may be calculated to group the mass spectrum data into new categories, in accordance with embodiments.

Intra-optimal correlation between two-different categories may be zero or around zero, meaning that they may be independent of one another, in accordance with embodiments. In embodiments, it may be difficult to obtain zero correlation from mass spectrums, especially for samples of similar profiles. Embodiments may utilize a clustering algorithm to find the lowest correlation between the initial clusters and re-group them into different clusters, if necessary.

Embodiments relate to the calculation of the cross-correlation coefficients ("CCC") between intra-elements and inter-elements. The intra-CCC between the elements in the same category should not be greater than the inter-CCC between different categories, in accordance with embodiments.

It will be obvious and apparent to those skilled in the art that various modifications and variations can be made in the embodiments disclosed. This, it is intended that the disclosed embodiments cover the obvious and apparent modifications and variations, provided that they are within the scope of the appended claims and their equivalents.

What is claimed is:

1. A method performed by at least one processor comprising:
   receiving mass spectrometer test data of a sample, wherein the mass spectrometer test data is generated by a MALDI-TOF MS machine;
   associating metadata information of a source of the sample to the mass spectrometer test data;
   selecting a subset of a sample reference library based on the associated metadata information, wherein the sample reference library comprises a plurality of sets of mass spectrometer reference data;
   matching the mass spectrometer test data with at least one set of the plurality of sets of mass spectrometer reference data of the selected subset of the sample reference library; and
   determining characteristic information of the source based on the known characteristics of the matched mass spectrometer reference data,
   wherein the selecting the subset of the sample reference library comprises determining overlap between the associated metadata information of the source and metadata information of the plurality of sets of mass spectrometer reference data,
   wherein the metadata information of the source and the metadata information of the plurality of sets of mass spectrometer reference data comprises a plurality of categories having parameters,
   wherein correlation between the plurality of categories is minimized in order to maximize independence of each of the plurality of categories,
   wherein the independence of each of the plurality of categories is determined by a dynamic threshold, and
   wherein the dynamic threshold for determining the independence of each of the plurality of categories is determined by at least one of artificial intelligence or deep learning algorithm.

2. The method of claim 1, wherein:
   the mass spectrometer test data has unknown characteristics; and
   the plurality of sets of mass spectrometer reference data has known characteristics.

3. The method of claim 1, wherein:
   the sample comprises biological molecules;
   the metadata information of the source comprises information about the source of the biological molecules; and
   the characteristic information of the source comprises a biological analysis info' ration of the source.

4. The method of claim 3, wherein the biological analysis information is a medical diagnosis of at least one of a human being, an animal, a plant, or a living organism.

5. The method of claim 3, wherein the characterization information of the source comprises at least one disease parameter.

6. The method of claim 5, wherein the at least one disease parameter is a correlation of disease information to the source of the biological molecules.

7. The method of claim 6, wherein the disease information relates to a disease and the disease information comprises at least one parameter or sub-parameter relating to at least one of:
   a name of the disease;
   a time stage of the disease;
   a type of the disease;
   a sub-type of the type of the disease;
   severity of the disease; or
   information relating to the disease.

8. The method of claim 3, wherein the characterization information comprises at least one non-disease parameter.

9. The method of claim 8, wherein the at least one non-disease parameter comprises attributes of the source.

10. The method of claim 8, wherein the at least one non-disease parameter comprises at least one of:
    an indication of a sex of the source;
    an indication of an age of the source;
    an indication of a disease history of the source;
    an indication of a family disease history of the source;
    an indication of a smoking history of the source;
    an indication of life habits of the source;
    an indication of a drinking history of the source;
    an indication of sugar levels of the source; and indication of cholesterol levels of the source; or
information relating to the source.

11. The method of claim 8, wherein the wherein the at least one non-disease parameter comprises at least one sub-parameter describing at least one attribute of the at least one non-disease parameter.

12. The method of claim 1, wherein the independence of each of the plurality of categories is based on at least one of a minimum independence threshold, a correlation coefficient index, a cross correlation index, a relative standard deviation analysis, or a distinction threshold to obtain a predetermined degree of diagnostic accuracy.

13. The method of claim 1, wherein the independence of each of the plurality of categories is determined based on a relative standard deviation value.

14. The method of claim 13, wherein the relative standard deviation value is at least one of minimized or optimized to maximize at least one of reproducibility or accuracy.

15. The method of claim 1, wherein the independence of each of the plurality of categories optimizes the selecting the subset of the sample library.

16. The method of claim 15, wherein the subset of the sample library is optimized by at least one of minimizing the size of the subset of the sample library or maintaining a predetermined degree of diagnostic accuracy.

17. The method of claim 15, wherein the subset of the sample library is optimized by eliminating irrelevant sets of the plurality of sets of mass spectrometer reference data.

18. The method of claim 17, wherein the eliminating irrelevant sets of the plurality of sets of mass spectrometer reference data comprises clustering categories of the plurality of categories that are not sufficiently independent to minimize size of the sample library.

19. The method of claim 18, wherein the clustering comprises:
determining at least one cross-correlation coefficient between at least two of the plurality of categories; and
if the at least one cross-correlation coefficient is greater than a predetermined threshold for the at least two of the plurality of categories, then clustering the at least two of the plurality of categories together to minimize the size of the sample library.

20. The method of claim 19, wherein the clustering categories comprises intra-category clustering at least two subcategories of one of the plurality of categories.

21. The method of claim 20, wherein the clustering categories comprises inter-category clustering of at least two subcategories of different categories of the plurality of categories.

22. The method of claim 21, wherein the predetermined threshold of the at least one cross-correlation coefficient is greater for intra-category clustering than for inter-category clustering.

23. The method of claim 17, wherein the irrelevant sets comprise sets of mass spectrometer reference data which have a risk of false positive or false negative output results based on the associated metadata information of the source.

24. The method of claim 17, wherein the irrelevant sets comprise sets of mass spectrometer reference data which are mutually exclusive to the associated metadata information.

25. The method of claim 1, wherein the correlation between the plurality of categories is determined from at least one of artificial intelligence or a deep learning algorithm.

26. The method of claim 21, the correlation between the plurality of categories is minimized to optimize at least one of diagnosing, screening, or identifying a medical condition.

27. The method of claim 1, wherein:
the mass spectrometer test data comprises a mass-to-charge profile output of a mass spectrometer;
the plurality of sets of mass spectrometer reference data comprises a plurality of mass-to-charge profiles of reference samples stored in the sample reference library; and
the matching comprises comparing the mass-to-charge profile of the mass spectrometer test data with the plurality of mass-to-charge profiles of the reference samples.

28. The method of claim 27, wherein the matching comprises deciding to match the mass spectrometer test data with a set of the plurality of sets of mass spectrometer reference data if there is substantially similar mass-to-charge profiles.

29. The method of claim 28, wherein the deciding to match the substantially similar mass-to-charge profiles is performed according to predetermined thresholds.

30. The method of claim 28, wherein the deciding to match the substantially similar mass-to-charge profiles is performed according to dynamic thresholds.

31. The method of claim 30, wherein the dynamic thresholds for the deciding to match the substantially similar mass-to-charge profiles are determined by at least one of artificial intelligence or deep learning algorithms.

32. The method of claim 1, wherein the sample reference library is stored in at least one of the MALDI-TOF MS machine, a hard drive, or a cloud database.

33. A system comprising:
at least one processor;
a receiving unit configured to receive mass spectrometer test data of a sample using the at least one processor;
an associating unit configured to associate metadata information of a source of the sample to the mass spectrometer test data using the at least one processor;
a selecting unit configured to select a subset of a sample reference library based on the associated metadata information using the at least one processor, wherein the sample reference library comprises a plurality of sets of mass spectrometer reference data;
a matching unit configured to match the mass spectrometer test data with at least one set of the plurality of sets of mass spectrometer reference data of the selected subset of the sample reference library using the at least one processor; and
a determining unit configured to determine characteristic information of the source based on the known characteristics of the matched mass spectrometer reference data using the at least one processor,
wherein the selecting unit selects the subset of the sample reference library by determining overlap between the associated metadata information of the source and metadata information of the plurality of sets of mass spectrometer reference data,
wherein the metadata information of the source and the metadata information of the plurality of sets of mass spectrometer reference data comprises a plurality of categories having parameters,
wherein correlation between the plurality of categories is minimized in order to maximize independence of each of the plurality of categories,
wherein the independence of each of the plurality of categories is determined by a dynamic threshold, and wherein the dynamic threshold for determining the independence of each of the plurality of categories is determined by at least one of artificial intelligence or deep learning algorithm.

34. A computer program product, comprising a computer readable hardware storage device having computer readable program code stored therein, said program code containing instructions executable by one or more processors of a computer system to implement a method of assessing damage to an object, said method comprising:

receiving mass spectrometer test data of a sample;

associating metadata information of a source of the sample to the mass spectrometer test data;

selecting a subset of a sample reference library based on the associated metadata information, wherein the sample reference library comprises a plurality of sets of mass spectrometer reference data;

matching the mass spectrometer test data with at least one set of the plurality of sets of mass spectrometer reference data of the selected subset of the sample reference library; and determining characteristic information of the source based on the known characteristics of the matched mass spectrometer reference data, wherein the selecting the subset of the sample reference library comprises determining overlap between the associated metadata information of the source and metadata information of the plurality of sets of mass spectrometer reference data, wherein the metadata information of the source and the metadata information of the plurality of sets of mass spectrometer reference data comprises a plurality of categories having parameters, wherein correlation between the plurality of categories is minimized in order to maximize independence of each of the plurality of categories, wherein the independence of each of the plurality of categories is determined by a dynamic threshold, and wherein the dynamic threshold for determining the independence of each of the plurality of categories is determined by at least one of artificial intelligence or deep learning algorithm.

35. The method of claim 27, wherein the mass-to-charge profile comprises data in units of time-of-flight.

* * * * *